US010254727B2

(12) United States Patent
Williams et al.

(10) Patent No.: US 10,254,727 B2
(45) Date of Patent: Apr. 9, 2019

(54) FEEDBACK CONTROL FOR A PERSON SUPPORT APPARATUS WITH A MATTRESS REPLACEMENT SYSTEM AND METHODS FOR AUTOMATICALLY PAUSING A TURN AND HOLD OPERATION

(71) Applicant: Hill-Rom Services, Inc., Batesville, IN (US)

(72) Inventors: Joshua A. Williams, West Harrison, IN (US); Nicholas C. Batta, Batesville, IN (US); Gregory J. Shannon, Indianapolis, IN (US); Andrew Robert Kerr, Cincinnati, OH (US)

(73) Assignee: Hill-Rom Services, Inc., Batesville, IN (US)

( * ) Notice: Subject to any disclaimer, the term of this patent is extended or adjusted under 35 U.S.C. 154(b) by 392 days.

(21) Appl. No.: 15/170,300

(22) Filed: Jun. 1, 2016

(65) Prior Publication Data

US 2016/0353900 A1   Dec. 8, 2016

Related U.S. Application Data

(60) Provisional application No. 62/171,052, filed on Jun. 4, 2015.

(51) Int. Cl.
*G05B 15/02* (2006.01)
*A61G 7/10* (2006.01)
(Continued)

(52) U.S. Cl.
CPC ............ *G05B 15/02* (2013.01); *A61G 7/001* (2013.01); *A61G 7/1021* (2013.01); *G16H 40/40* (2018.01)

(58) Field of Classification Search
CPC ..... A47C 27/08; A47C 27/081; A47C 27/082; A47C 27/083; A47C 27/10; A61G 7/001; A61G 7/002; A61G 7/008; A61G 7/015; A61G 7/018; A61G 7/05; A61G 7/0525; A61G 7/057; A61G 7/0573; A61G 7/05769; A61G 7/05776; A61G 7/10; A61G 7/1013; A61G 7/1021
See application file for complete search history.

(56) References Cited

U.S. PATENT DOCUMENTS

| 2011/0047703 | A1* | 3/2011 | Tarsaud | ............... | A61G 7/001 5/607 |
| 2015/0164236 | A1* | 6/2015 | Driscoll, Jr. | ......... | A47C 27/082 5/713 |

(Continued)

*Primary Examiner* — Eric J Kurilla
(74) *Attorney, Agent, or Firm* — Dinsmore & Shohl LLP

(57) ABSTRACT

A method for triggering a pause event in a turn and hold operation applied to a mattress replacement system of a person support apparatus may include inflating at least one air bladder in only one of a right side portion and a left side portion of the mattress replacement system; detecting, automatically with at least one sensor, a force applied to at least one of a frame of the personal support apparatus and the at least one air bladder as the at least one air bladder is inflated; determining, automatically with a microcontroller communicatively coupled to the at least one sensor, if the force applied has a force duration that is greater than a threshold force duration to trigger the pause event; and discontinuing inflation of the at least one air bladder when the pause event is triggered.

16 Claims, 4 Drawing Sheets

(51) Int. Cl.
*A61G 7/00* (2006.01)
*G16H 40/40* (2018.01)

(56) References Cited

U.S. PATENT DOCUMENTS

2016/0058641 A1* 3/2016 Moutafis ................ A47C 27/10
  5/672
2018/0153310 A1* 6/2018 Thomas ............... A47C 27/061

* cited by examiner

FEEDBACK CONTROL FOR A PERSON SUPPORT APPARATUS WITH A MATTRESS REPLACEMENT SYSTEM AND METHODS FOR AUTOMATICALLY PAUSING A TURN AND HOLD OPERATION

CROSS REFERENCE To RELATED APPLICATIONS

The present specification claims priority to U.S. Provisional Patent Application Ser. No. 62/171,052, filed Jun. 4, 2015 and entitled "FEEDBACK CONTROL FOR A PERSON SUPPORT APPARATUS WITH A MATTRESS REPLACEMENT SYSTEM AND METHODS FOR AUTOMATICALLY PAUSING A TURN AND HOLD OPERATION," the entirety of which is incorporated by reference herein.

TECHNICAL FIELD

The present specification generally relates to person support apparatuses for use in healthcare facilities and, more specifically, to person support apparatuses with mattress replacement systems or frames, and methods for controlling the same.

BACKGROUND

Individuals in health care facilities may rest on person support apparatuses that include mattress replacement systems. Caregivers may at times need to turn a resting individual to a different position and hold the resting individual at that position for a period of time. Person support apparatuses may have control boxes that include controls to start a turn and hold operation.

A need exists for alternative methods for turning and holding individuals resting on person support apparatuses in acute care settings, and apparatuses for use in performing such methods.

SUMMARY

In one embodiment, a method for triggering a pause event in a turn and hold operation applied to a mattress replacement system of a person support apparatus may include inflating, automatically with a pump, at least one air bladder in only one of a right side portion and a left side portion of the mattress replacement system, wherein an inflation of the other of the right side portion and the left side portion is not increased; detecting, automatically with at least one sensor, a force applied to at least one of a frame of the person support apparatus and the at least one air bladder as the at least one air bladder is inflated; determining, automatically with a microcontroller communicatively coupled to the at least one sensor, if the force applied to at least one of the frame and the at least one air bladder has a force duration that is greater than a threshold force duration to trigger the pause event; and discontinuing inflation of the at least one air bladder when the pause event is triggered.

In another embodiment, a system may include a person support apparatus including at least one sensor, a frame, and a mattress, the mattress including a plurality of air bladders, wherein at least one first sensor is disposed in at least one of the mattress and the frame, and a processor communicatively coupled to a non-transitory computer storage medium and the sensor, wherein the non-transitory computer storage medium stores instructions. When the instructions are executed by the processor, the instructions may cause the processor to inflate, automatically with a pump, at least one air bladder in only one of a right side portion and a left side portion of the mattress replacement system, wherein an inflation of the other of the right side portion or the left side portion is not increased, detect, automatically with the at least one sensor, a force applied to at least one of a frame of the person support apparatus and the at least one air bladder as the at least one air bladder is inflated, determine, automatically with the processor communicatively coupled to the at least one sensor, if the force applied to at least one of the frame and the at least one air bladder has a force duration that is greater than a threshold force duration to trigger a pause event, and discontinue inflation of the at least one air bladder when the pause event is triggered.

These and additional features provided by the embodiments described herein will be more fully understood in view of the following detailed description, in conjunction with the drawings.

BRIEF DESCRIPTION OF THE DRAWINGS

The embodiments set forth in the drawings are illustrative and exemplary in nature and not intended to limit the subject matter defined by the claims. The following detailed description of the illustrative embodiments can be understood when read in conjunction with the following drawings, where like structure is indicated with like reference numerals and in which:

DETAILED DESCRIPTION

In embodiments, a method for triggering a pause event in a turn and hold operation applied to a mattress replacement system of a person support apparatus, which includes a frame that supports the mattress replacement system, may include positioning a plurality of air bladders in both a left side and a right side of the mattress replacement system and disposing at least one first sensor in at least one of the mattress and the frame. The left side and the right side of the mattress replacement system are divided along a sagittal line. The method may further include initiating the turn and hold operation such that a selected set of the plurality of air bladders on a select one of the left side or the right side of the mattress replacement system begin to inflate and angle the mattress with respect to a normal resting position of the mattress and then pausing the turn and hold operation.

For example, to pause the turn and hold operation prior to a final position being reached, a force may be applied on the at least one first sensor to transmit an overpressure signal. When the force is applied for a set period of time while the overpressure signal is being transmitted, a pause event signal is generated. Based on the pause event signal, a microcontroller may automatically activate a pause in the turn and hold operation prior to the final position being reached such that the selected set of the plurality of air bladders are held at a paused level of inflation that is less than the level of inflation associated with the final position.

The methods and apparatuses described herein address a difficulty a caregiver may have when attempting to pause a turn and hold operation of a mattress replacement system of a person support apparatus when simultaneously stabilizing a person resting on the mattress replacement system. The methods and apparatuses described herein thus assist a caregiver with pausing a turn and hold operation without leaving the side of a person resting on a person support apparatus such that the caregiver may be able to continue, for example, holding and supporting the resting person while pausing the turn and hold operation. Methods and apparatuses for turning and holding individuals resting on person support apparatuses such as in acute care settings are further described in embodiments herein.

Figure 1:
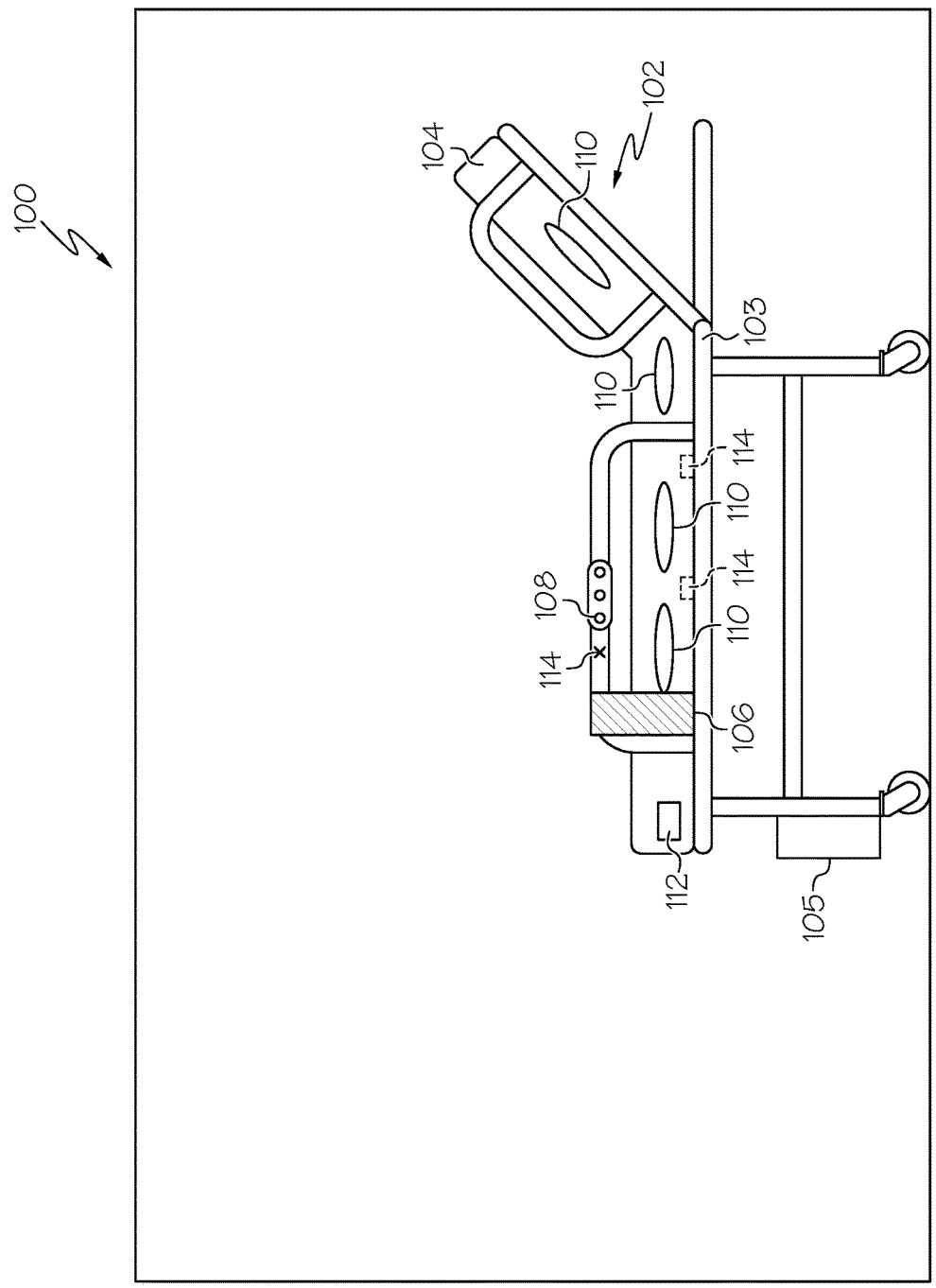
FIG. 1 schematically depicts a person support apparatus with a mattress replacement system, according to one or more embodiments shown and described herein.

Referring now to FIG. 1, a room 100 in an acute care setting, such as a hospital, includes a person support apparatus 102. The person support apparatus 102, for example, may be a person support apparatus similar to the HILL-ROM® ENVISION®, TOTALCARE® P500, and/or HILL-ROM® DUO® 2 beds commercially available from HILL-ROM® or Hill-Rom Services, Inc. of Batesville, Ind., for example. However, it should be understood that other person support apparatuses compatible with the methods described herein are contemplated and possible.

The person support apparatus 102 includes a frame 103 and a mattress replacement system 104. The mattress replacement system 104 includes a plurality of air bladders 110, with a first portion of air bladders 110 on a first half of the mattress replacement system 104 and a second portion of air bladders 110 on a second half of the mattress replacement system 104. For example, the first half of the mattress replacement system 104 may be a left side of the mattress replacement system 104 with respect to a sagittal line, axis, or plane of the mattress replacement system 104 (i.e., the line, axis, or plane extending from the head of the person support apparatus 102 to the foot of the person support apparatus 102 and bisecting the person support apparatus 102 into first and second halves). And the second half of the mattress replacement system 104 may be a right side of the mattress replacement system 104 with respect to the sagittal line, axis, or plane of the mattress replacement system 104.

In embodiments, at least a first sensor is disposed in at least one of the mattress replacement system 104 and the frame 103 of the person support apparatus 102. In embodiments, a plurality of sensors may be included in the person support apparatus 102. In embodiments, the sensors 112, and/or 114 may be disposed within, as part of, incorporated into, and/or integrated with the person support apparatus 102 and/or a person support apparatus component such as a mattress and/or frame. In embodiments, the sensors 112 and 114 are communicatively coupled to one another.

In some embodiments, the person support apparatus 102 may include load sensors 114 disposed between the frame 103 and the mattress replacement system 104. Additionally or alternatively, one or more load sensors 114 may be disposed along or within exterior portions of frame 103 such as a side rail. The various components of frame 103 may work in conjunction with one another to initiate and perform a turn and hold operation, as described in more detail below with respect to FIG. 2.

Additionally or alternatively, the mattress replacement system 104 may include one or more sensors 112 for detecting pressure changes within the air bladders 110. In embodiments, the sensors 112 may be pressure sensors associated with one or more air bladders 110 such as sensors 112A-112C of FIG. 2. For example, referring to FIG. 2, sensors 112 may be sensors 112A disposed within the one or more air bladders 110. Additionally or alternatively, sensors 112 may be sensors 112B attached to one or more air bladders 110. Additionally or alternatively, sensors 112 may be sensors 112C disposed along an air passage conduit between the one or more air bladders 110 and a valve 206, described further below.

The sensors 112A-112C, for example, may be used to capture readings, such as air pressure readings, from the one or more air bladders 110 to measure fluctuations or changes of the pressure of the air bladders and these air pressure readings may be utilized to determine if the air pressure within the one or more air bladders 110 surpasses a threshold for a predetermined period of time. The one or more sensors 112 may be, for example, pressure transducers attached to and/or within the air bladders 110 that detect a change in pressure that surpasses a threshold for a set amount of time to activate a pause trigger.

Additionally or alternatively, the at least a first sensor may be a sensor 112 disposed in the mattress replacement system 104 of the person support apparatus 102. Sensor 112 in a mattress replacement system or mattress of the person support apparatus 102 may be, for example, a capacitive sensor that senses a level of capacitance between two metallic sheets or plates in the mattress. If a pressure is applied to a top metallic sheet, for example, it will become closer to the bottom metallic sheet such that a changeable distance between the pair of sheets is reduced and a reduction in capacitance would be measured by sensor 112.

Additionally or alternatively, the at least a first sensor may be a sensor 114 such as a load sensor disposed in the frame 103 of the person support apparatus 102 and/or between the frame 103 and the mattress replacement system 104. The sensor 114 may be part of a scale system to sense loads and measure applied forces or weights.

Referring again to FIG. 1, the frame 103 may include a control box 105 at a foot portion of the person support apparatus 102, a graphical user interface (GUI) 106, a pendent 108, and one or more load sensors 114. In some embodiments, the graphical user interface 106 may be a Graphical Caregiver Interface ("GCI®") commercially available from HILL-ROM® or Hill-Rom Services, Inc. of Batesville, Ind., for example. In some embodiments, the pendent 108 may be a handheld remote control device to control operations of the person support apparatus 102. The caregiver may be able to activate a pause turn and hold or pause turn assist event via a mechanism or button provided on the graphical user interface 106 and/or the pendent 108.

Figure 2:
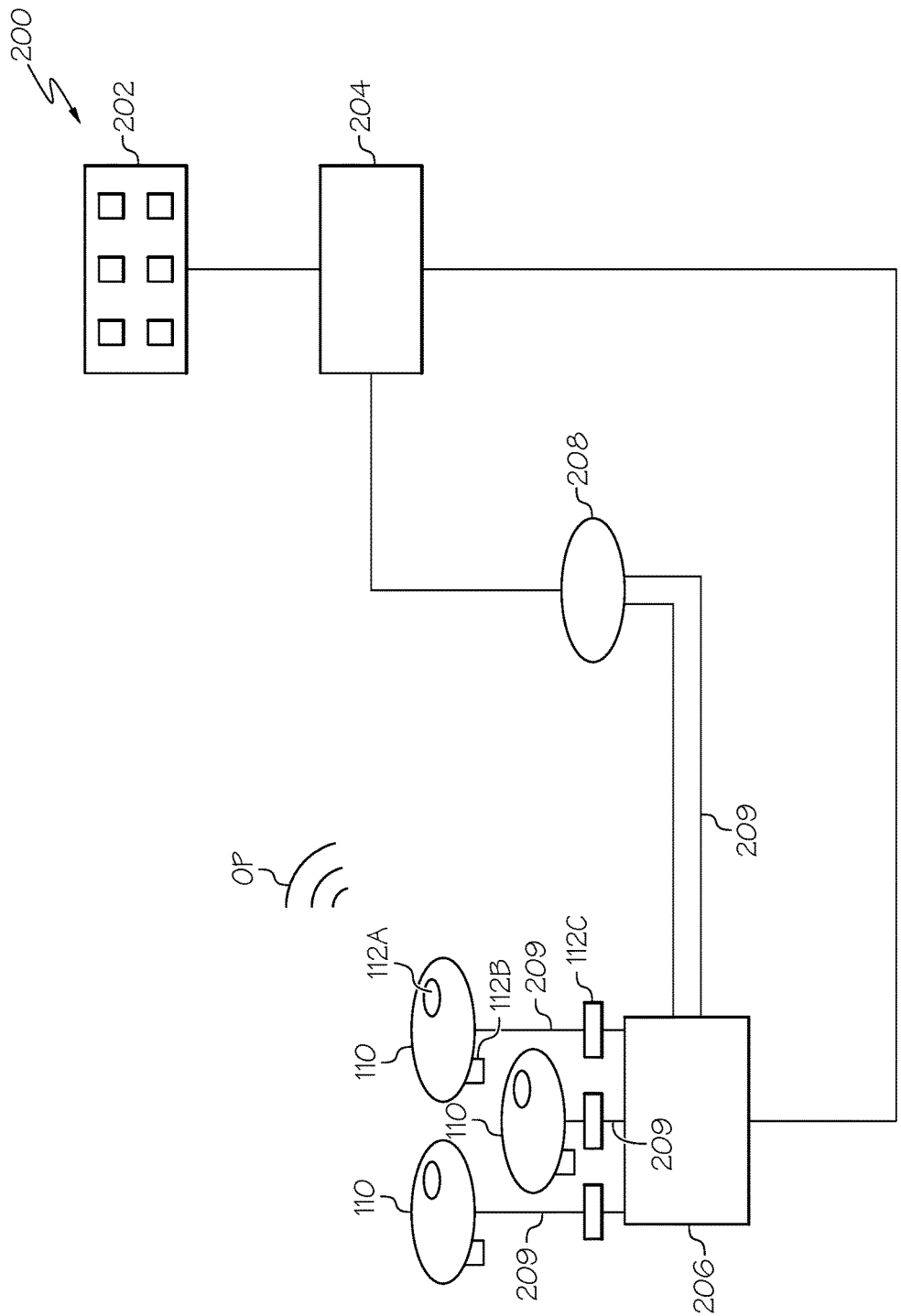
FIG. 2 schematically depicts a system for implementing a method to automatically pause a turn and hold operation according to one or more embodiments described herein.

As shown in FIG. 2, the mattress replacement system 104 includes a system 200 for selectively inflating and deflating the air bladders 110. The system 200 includes the air bladders 110 which are fluidly coupled to a pump 208 with air passage conduit(s) 209 and at least one valve 206. Each of the pump 208 and valve 206 are communicatively coupled to a microcontroller 204. The microcontroller 204 includes a processor and a non-transitory storage medium such as a memory containing readable and executable instructions which, when executed by the processor, actuate the valve 206 and pump 208 to selectively inflate or deflate the air bladders 110. The system 200 also includes the sensors 112 which may be communicatively coupled to the microcontroller 204 either by wires (not shown) or wirelessly. The microcontroller 204 is also communicatively coupled to a graphical user interface, such as GUI 202, which may be a pendent controller, or an interface fixed to the person support apparatus 102. The microcontroller 204 and the GUI 202 are able to exchange electrical signals therebetween to facilitate operation of at least the valve 206 and pump 208 and selective inflation/deflation of the air bladders 110.

Figure 3:
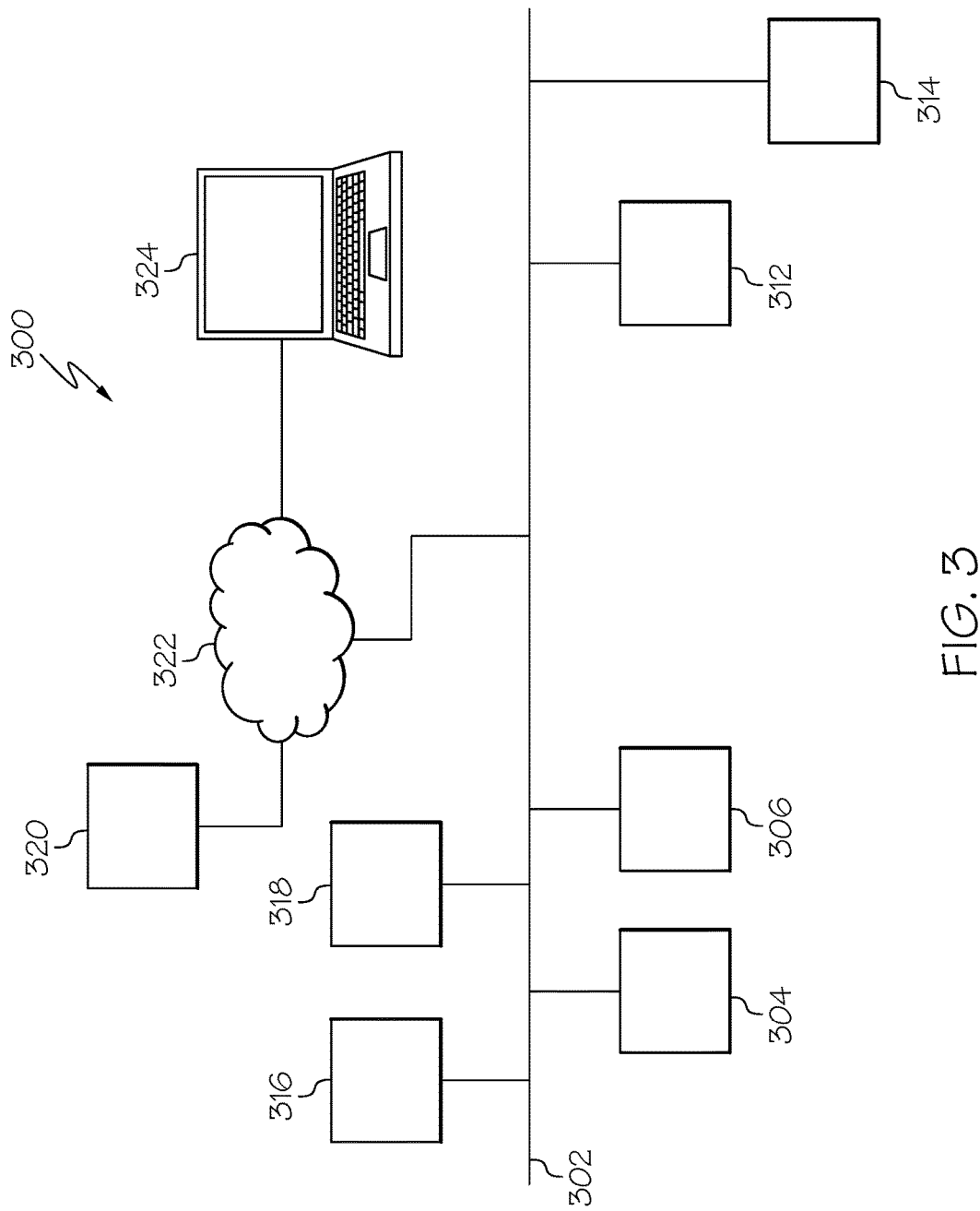
FIG. 3 schematically depicts a communication block diagram including components to assist to implement a computer and software-based method to automatically pause a turn and hold operation according to one or more embodiments described herein.

The system 200 may be implemented with electrical components such as those shown within a communication block diagram 300 of FIG. 3. Referring to FIG. 3, for example, the communication block diagram 300 shows components that implement a computer and software-based method to automatically pause a turn and hold operation, such as exemplary person support apparatus 102. The components are usable along with a graphical user interface (GUI), which may be at least one of the control box 105 and the GUI 106, for example. The diagram 300 includes a communication path 302, one or more processors 304 that may be associated with the microcontroller 204, for example, a memory component 306, a sensory input 312, a storage or database 314, a person support apparatus display 316, a network interface hardware 318, a network 322, a server 320, and at least a computer 324. The various components of the diagram 300 are communicatively coupled and interact together.

Referring again to FIG. 2, the system 200 for performing a turn and hold operation includes the plurality of air bladders 110 disposed in the mattress replacement system 104 and oriented along a sagittal line of the mattress replacement system 104 into a left side portion and a right side portion, as described herein. The GUI 202, provides a user, such as a care giver, with the option of beginning a turn and hold or turn assist operation for a pre-determined hold period of time. When such an option is selected, the microcontroller 204 transmits a signal to valve 206, actuating the valve 206 and allowing for an ingress of air from pump 208 through air passage conduit 209, thereby inflating one of a selected left side portion or right side portion of the plurality of air bladders 110. For example, if the left side portion is selected, the plurality of air bladders 110 on the left side portion of the mattress replacement system 104 begin to inflate while the plurality of air bladders in the right side portion of the mattress replacement system 104 may remain at an initial level of inflation or, alternatively, may be slightly deflated to further enhance the height difference between the left side portion and the right side portion of the mattress replacement system.

Inflation of the air bladders associated with the left side portion causes the left side portion of the mattress replacement system 104 to begin to angle with respect to the right side portion. As the angle of inclination increases, a person resting on the mattress replacement system 104 begins to turn toward the right side portion of the mattress replacement system 104. Alternatively, the right side portion may be selected such that the plurality of air bladders 110 on the right side portion of the mattress replacement system 104 begin to inflate while the plurality of air bladders 110 on the left side portion of the mattress replacement system 104 remain in the initial, normal level resting position or are slightly deflated.

When the turn and hold operation is complete (i.e., when a pre-determined level of inflation of the selected air bladders 110 is reached) the GUI 202 and microcontroller 204 hold the mattress replacement system 104 at its angled position for the pre-determined hold period of time. The hold time may be, for example, 30 minutes, or in the range of from about 15 minutes to about 45 minutes. While the hold time may be automatically pre-set, in some embodiments, a user may determine and select a hold time. The angle of inclination for the final hold position for a selected side of the mattress replacement system 104 may be, for example, in a range from about 10 degrees to about 45 degrees from horizontal. After the determined hold period of time is complete, the microcontroller 204 may cause an egress of air from the selected side of air bladders 110 through the valve 206. Such an egress action deflates the selected side of air bladders 110 until the initial, normal level resting position for the selected side of air bladders 110 is reached such that the left side portion and the right side portion of the plurality of air bladders 110 are generally level with one another.

Still referring to FIGS. 1 and 2, the embodiments of the mattress replacement system described herein also include a pause functionality which allows the inflation of the selected side of air bladders 110 to be paused prior to reaching the final hold position. For example, in embodiments, sensor 112 is a pressure sensor associated with an air bladder, as described above. Pressure may be applied by the caregiver to the air bladder as the air bladder is being inflated, such as by pressing down on the air bladder with a hand, forearm or elbow, causing an overpressure within the air bladder. When the overpressure is maintained for a predetermined amount of time, such as in a range from about 3 seconds to about 15 seconds, or in a range of from about 5 seconds to about 10 seconds, the output signal from the sensor 112 to the microprocessor categorized by the microprocessor as an overpressure signal OP. For example, if the signal occurs for a duration of time that is greater than a threshold force duration of time, the microcontroller 204 categorizes the signal as an overpressure signal OP and activates a pause turn assist event causing an automated and effectively real-time pause in the turn and hold operation with respect to a selected set of air bladders 110 of a selected side of the mattress replacement system 104 by holding the air bladders at a paused level of inflation as described above. Additionally or alternatively, sensor 112 may be an accelerometer to sense such a fluctuation in pressure for a set amount of time surpassing a threshold duration to activate a pause trigger event signal.

Additionally or alternatively, in embodiments, if sensor 114 is a load sensor and if a load such as a pressure is applied to sensor 114 for the set amount of time as described above, the microprocessor may categorize the output of the sensor 114 as an overpressure signal OP that causes the microcontroller 204 to output a pause event signal that causes a pause in the turn and hold operation to be triggered such that the selected set of air bladders 110 are paused at a paused level of inflation.

Figure 4:
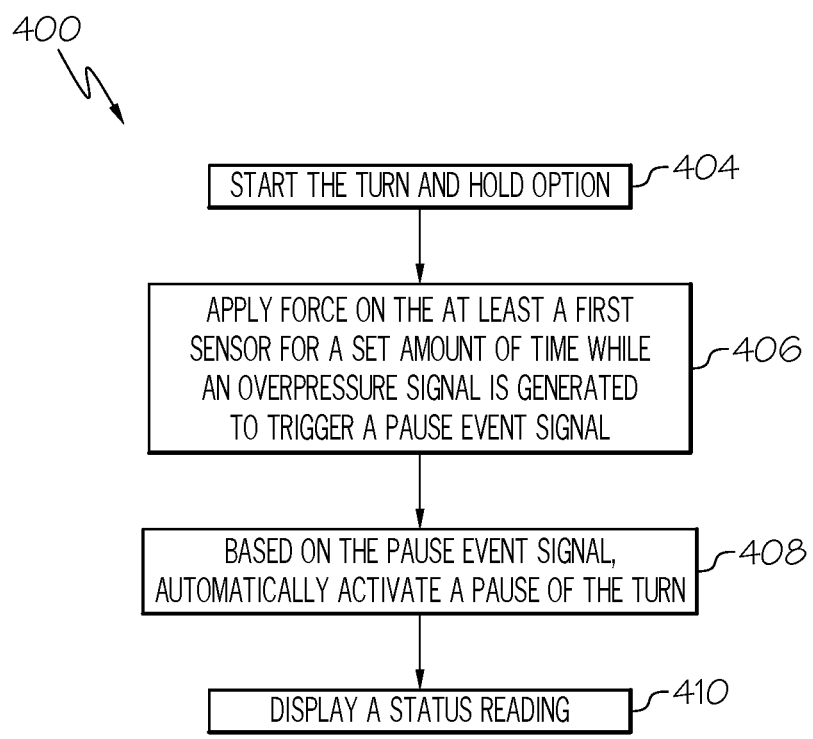
FIG. 4 schematically depicts an exemplary method of automatically pausing a turn and hold operation according to one or more embodiments described herein.

Referring now to FIG. 4, a flow chart of an exemplary method 400 for triggering a pause event in a turn and hold operation with a mattress replacement system is schematically depicted. As note hereinabove, a caregiver may wish to pause the turn and hold operation prior to the selected side of air bladders reaching the final level of inflation.

In step 404, the turn and hold option may be started as described above with respect to FIG. 2. In step 406, an operator, such as a caregiver, applies a force to the mattress replacement system to increase the pressure in the selected side of air bladders. The increase in pressure is detected by at least one sensor 112 and/or 114, which outputs a signal to the microcontroller 204 which, in turn, determines if the signal is an overpressure signal OP based on the duration of the signal. If the signal is an overpressure signal OP, the microcontroller 204 discontinues or pauses the turn and hold operation. For example, the caregiver may apply a force on the selected side of air bladders 110 that cause associated sensors 112A, 112B, and/or 112C to transmit a signal to the microcontroller 204. In one embodiment, the time duration of the signal output from the sensor is utilized by the microcontroller 204 to determine if an overpressure exists and if a pause in the turn and hold operation is desired. Once the overpressure signal OP is registered (i.e., once the microcontroller 204 determines that a pause in the turn and hold operation is desired), the microcontroller 204 may output a pause event signal which causes the inflation of the selected air bladders to be discontinued. Alternatively or additionally, once the overpressure signal OP is registered by the microcontroller 204, the microcontroller 204 may isolate the selected air bladders from the pump 208 with the valve 206 and/or discontinue operation of the pump 208. For example, in one embodiment, if the overpressure signal OP is transmitted for a set amount of time, the microcontroller 204 registers that the caregiver desires to pause the turn and hold operation and, as such, the microcontroller 204 transmits a pause event signal to automatically pause the turn and hold operation as described below. The set amount of time may be, for example, in the range of from about 3 seconds to 15 seconds, or in the range of from about 5 seconds to 10 seconds.

In step 408, based on the pause event signal, a pause of the turn and hold of a selected side of the mattress replacement system 104 is automatically activated. For example, referring to FIG. 2, the pause event trigger signal from the microcontroller 204 may cause the air pump 208 to stop pumping air through air passage conduit 209 toward and through valve 206 and/or may close valve 206.

An algorithm may be applied by the microcontroller 204 that causes the microcontroller 204 to receive the signal from the sensor and, if the signal is an overpressure signal OP and a set amount of time has elapsed after receiving the overpressure signal OP, the microcontroller 204 triggers a pause turn event signal. The pause turn event signal is transmitted by the microcontroller 204 to pause the inflation of the selected air bladders 110 on either a selected right or left side of the mattress replacement system 104 at a paused level of inflation. The caregiver may maintain the person on the person support apparatus 102 at the paused position until pressure is again applied to the sensors 112, and/or 114 for a set amount of time to de-trigger the pause event and to either continue the turn until the hold position is reached or return the mattress holding the resting individual to a normal resting position. Alternatively or additionally, the caregiver may activate a separate signal to deflate the air bladders 110 and return the mattress holding the resting individual to a normal resting position. For example, in embodiments, after pausing the turn and hold operation, or before the determined hold period of time is complete, a caregiver may activate a return to normal feature on the control box 105 to deflate the bladders as described above with respect to FIG. 2 and allow them to return to their normal, resting mode and level.

In some embodiments, in step 410, a status reading of at least one of the at least one sensor and the turn and hold operation is displayed on a graphical user interface. For example, a status reading may be displayed on a GUI such as GUI 202. In embodiments, a first report of the status of the turn and hold operation is displayed on a graphical user interface and may indicate angle with respect to the normal resting position, whether a pause has been activated, and a period of time the turn and hold operation has been operating. Further, one or more alerts may be generated when the pause event signal is generated that pauses the turn and hold operation. A user may then have an additional indication that the pause request was received and is being automatically activated to assist the user or caregiver with support in caring for an individual on the person support apparatus 102. In some embodiments, one or more alerts may be generated when at least one of the turn and hold operation is initiated, the pause in the turn and hold operation is automatically activated, and the hold position is reached.

Thus, through the methods and apparatuses described herein, a caregiver may maintain contact with an individual resting in the person support apparatus 102 while a turn and hold operation is ongoing and when the caregiver wishes to activate a pause turn assist functionality. For example, while maintaining a grip by both hands on the resting individual, the caregiver may use an elbow to apply force to the sensor 112, 112A, 112B, 112C, and/or 114 for a period of 5 seconds to activate the pause trigger and thus automatically activate a pause turn event such that the selected air bladders 110 stop inflating and are held in a paused, inflated state prior to reaching a level of inflation associated with the final hold position. Or the caregiver may maintain a one-handed grip on the patient with a first hand while applying a force or pressure on the sensor 112, 112A, 112B, 112C, and/or 114 via a second hand. Regardless of the method of actuation, the systems described herein may effectively transform at least a selected set of air bladders into large sensors which can be manipulated to pause the turn and hold operation without having to leave the side of the patient.

It is noted that the terms "substantially" and "about" may be utilized herein to represent the inherent degree of uncertainty that may be attributed to any quantitative comparison, value, measurement, or other representation. These terms are also utilized herein to represent the degree by which a quantitative representation may vary from a stated reference without resulting in a change in the basic function of the subject matter at issue.

While particular embodiments have been illustrated and described herein, it should be understood that various other changes and modifications may be made without departing from the spirit and scope of the claimed subject matter. Moreover, although various aspects of the claimed subject matter have been described herein, such aspects need not be utilized in combination. It is therefore intended that the appended claims cover all such changes and modifications that are within the scope of the claimed subject matter.

What is claimed is:
1. A method for triggering a pause event in a turn and hold operation applied to a mattress replacement system of a person support apparatus, the method comprising:
    inflating, automatically with a pump, at least one air bladder in only one of a right side portion or a left side portion of the mattress replacement system, wherein an inflation of one or more air bladders of the other of the right side portion or the left side portion is not increased, wherein a plurality of air bladders including the at least one air bladder and the one or more air bladders are disposed within the right side portion and the left side portion of the mattress replacement system;
    detecting, automatically with at least one sensor, a force applied to at least one of a frame of the person support apparatus and the at least one air bladder as the at least one air bladder is inflated;
    determining, automatically with a microcontroller communicatively coupled to the at least one sensor, if the force applied to at least one of the frame and the at least one air bladder has a force duration that is greater than a threshold force duration to trigger the pause event; and discontinuing inflation of the at least one air bladder when the pause event is triggered.

2. The method of claim 1, wherein the threshold force duration is in a range of from 3 seconds to 15 seconds.

3. The method of claim 1, wherein the at least one sensor is at least one of a pressure transducer associated with the at least one air bladder, a capacitive sensor disposed in the mattress replacement system, and a load sensor disposed in the frame.

4. The method of claim 1, wherein the at least one sensor is a pressure transducer associated with the at least one air bladder and measures fluctuations of air pressure over a period of time.

5. The method of claim 1, further comprising generating one or more alerts when the pause event is triggered.

6. A system comprising:
- a person support apparatus including at least one sensor, a frame, and a mattress, the mattress including a plurality of air bladders, wherein the at least one sensor is disposed in at least one of the mattress and the frame; and
- a microcontroller comprising a processor communicatively coupled to a non-transitory computer storage medium and the at least one sensor, wherein the non-transitory computer storage medium stores instructions that, when executed by the processor, cause the processor to:
  - inflate, automatically with a pump, at least one air bladder in only one of a right side portion or a left side portion of the mattress, wherein an inflation of one or more air bladders of the other of the right side portion or the left side portion is not increased, wherein a plurality of air bladders including the at least one air bladder and the one or more air bladders are disposed within the right side portion and the left side portion of the mattress replacement system;
  - detect, automatically with the at least one sensor, a force applied to at least one of the frame of the person support apparatus and the at least one air bladder as the at least one air bladder is inflated;
  - determine, automatically with the microcontroller, if the force applied to at least one of the frame and the at least one air bladder has a force duration that is greater than a threshold force duration to trigger a pause event; and
  - discontinue inflation of the at least one air bladder when the pause event is triggered.

7. The system of claim 6, wherein the threshold force duration is in a range of from 3 seconds to 15 seconds.

8. The system of claim 6, wherein the threshold force duration is in a range of from 5 seconds to 10 seconds.

9. The system of claim 6, wherein the instructions further cause the processor to provide one or more alerts when at least one of the inflation is initiated and the inflation is discontinued.

10. The system of claim 6, wherein the instructions further cause the processor to provide one or more alerts when the pause event is triggered.

11. The system of claim 6, wherein the at least one sensor is at least one of a pressure transducer associated with the at least one air bladder, a capacitive sensor disposed in the mattress, and a load sensor disposed in the frame.

12. The system of claim 6, wherein the at least one sensor is a pressure transducer associated with the at least one air bladder and measures changes of air pressure associated with the applied force with respect to a pressure threshold.

13. The system of claim 6, wherein the at least one sensor is a load sensor disposed in the frame.

14. The system of claim 6, wherein the at least one sensor is a capacitive sensor disposed in the mattress that measures capacitive change associated with a changeable distance between a pair of plates, wherein the distance is changeable via an application of force on the capacitive sensor, and an output signal of capacitive change associated with the applied force is transmitted when a capacitive change threshold is surpassed.

15. The system of claim 6, wherein the instructions, when executed by the processor, cause the processor to resume the inflation after discontinuing the inflation until a hold position is reached and, after a hold time is reached while the mattress is in the hold position, to deflate the at least one air bladder to return the mattress back to a normal resting position.

16. The system of claim 6, wherein the instructions, when executed by the processor, cause the processor to deflate the at least one air bladder to return the mattress to a normal resting position after discontinuing inflation of the at least one air bladder when the pause event is triggered and after a hold time is reached.

* * * * *